(12) United States Patent
Sera

(10) Patent No.: US 6,271,878 B1
(45) Date of Patent: *Aug. 7, 2001

(54) PEELING DETECTOR FOR TUNNEL WALL

(75) Inventor: Yoshihiro Sera, Komaki (JP)

(73) Assignee: Mitsubishi Heavy Industries, Ltd., Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/925,715

(22) Filed: Sep. 9, 1997

(51) Int. Cl.[7] ....................................................... H04N 5/33
(52) U.S. Cl. ............................. 348/164; 374/57; 374/124; 250/341
(58) Field of Search ................................. 348/61, 82, 84, 348/85, 164; 702/34, 35, 40; 374/4, 5

(56) References Cited

U.S. PATENT DOCUMENTS

| | | | |
|---|---|---|---|
| 4,654,702 | * | 3/1987 | Tolino ................................... 348/84 |
| 4,722,001 | * | 1/1988 | Rohrich ................................. 348/84 |
| 4,913,558 | * | 4/1990 | Wettervik .............................. 348/84 |
| 4,988,210 | * | 1/1991 | Koshihara .............................. 374/5 |
| 5,709,469 | * | 1/1998 | White ..................................... 374/5 |
| 5,770,800 | * | 6/1998 | Jenkins .................................. 348/84 |

FOREIGN PATENT DOCUMENTS 5108796   4/1993   (JP) .

* cited by examiner

Primary Examiner—Chris Kelley
Assistant Examiner—Shawn S. An

(57) ABSTRACT

A peeling detector for a tunnel wall capable of rapidly inspecting the tunnel wall by effectively using infrared radiation is provided. The detector heats a tunnel wall 1 with a light emitting heater 4 while moving. An infrared camera 6 detects infrared radiation radiated by the wall after heating. Based on the quantity of the infrared energy, a difference in the temperature between peeled and normal portions induced by heating is grasped to evaluate whether the peeling of the tunnel wall 1 is present or not.

10 Claims, 8 Drawing Sheets

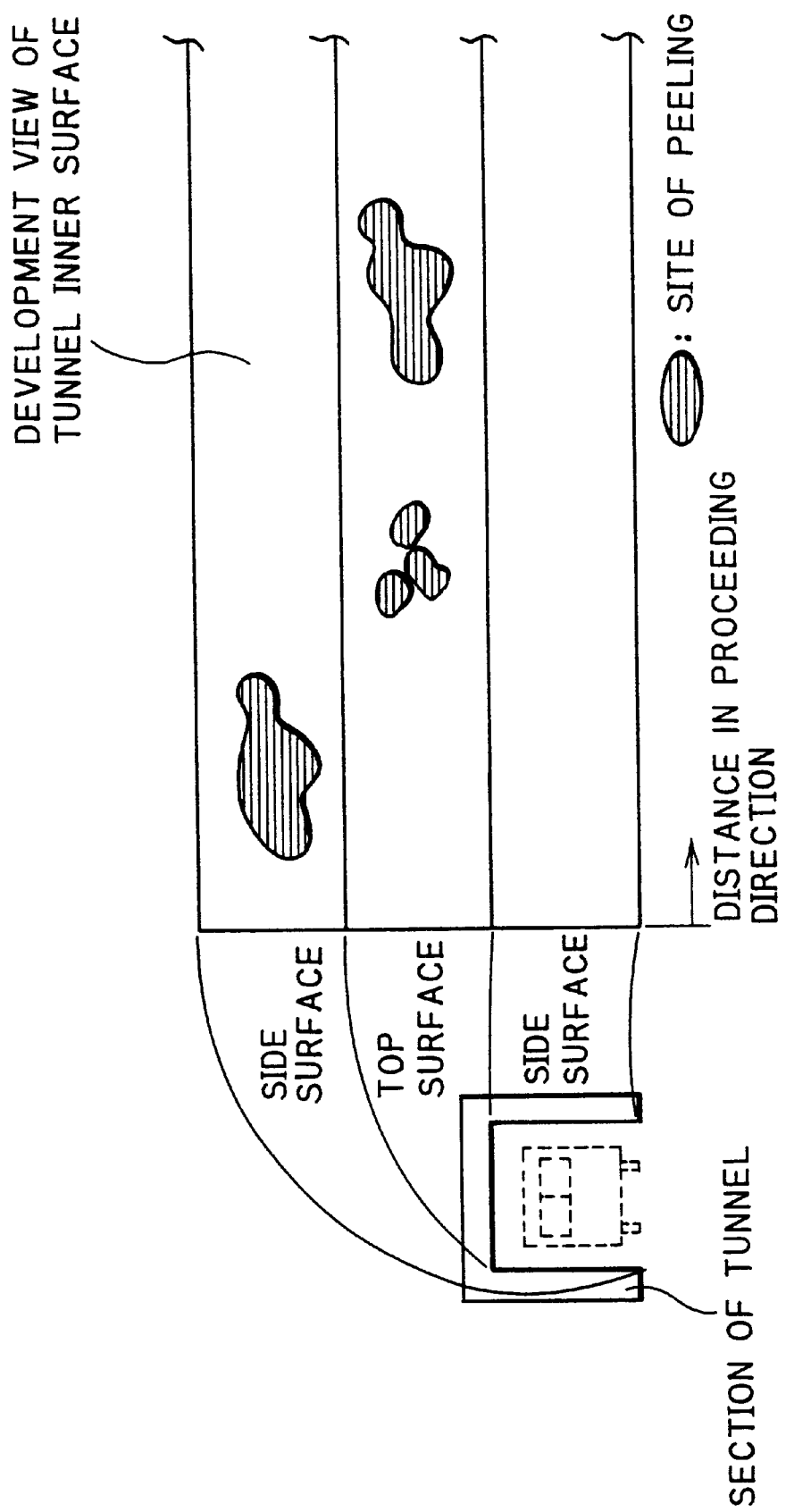

Fig. 4

○ Good △ Fair ✕ Poor

| Type of method | Outline | | Energy transfer efficiency | | Ease of heating during movement | | Overall evaluation | |
|---|---|---|---|---|---|---|---|---|
| Light emitting heater method | Light emitting heater / Wall / Light energy. Radiate light energy from light emitting heater to heat wall. | | ○ | A short distance between light emitting heater and wall can decrease midway transfer loss, thus making energy transfer efficiency high. | ○ | Heating is possible with distance from wall surface maintained, thus facilitating heating during movement. Because of large heat generation, relatively high speed movement is possible. | ○ | Excellent in both of energy transfer efficiency and ease of movement. |
| Warm air heater method | Warm air heater / Wall / Warm air. Direct warm air from warm air heater at wall to heat it. | | ✕ | Air is low in heat conductivity, increasing transfer loss between warm air and wall. | △ | Heating is possible with distance from wall surface maintained, thus facilitating heating during movement. Because of small heat conduction, moving speed is low. | △ | Poor in energy transfer efficiency. |
| Contact heating method | Contact heater / Wall surface. Bring contact heater into contact with wall to heat it. | | ○ | Contact heater of high heat conductivity material can decrease transfer loss, thus making energy transfer efficiency high. | ✕ | Since contact with wall surface is required, heating during movement is difficult. | △ | Poor in ease of movement. |

Fig. 8

| Item | Characteristic of peeling of tunnel wall surface | Detection limit of inventive detector | Effectiveness of inventive detector. | Grounds for estimation of detection limit. |
|---|---|---|---|---|
| Peeling area (diameter) | ø several cm to ø several cm | Minimum detectable peeling diameter : ø 20 cm or less | Sufficiently effective for judging whether to repair, because peeling of ø 50 cm or more should be repaired. | Peeling with thickness of 1 cm but having ø 20 cm or more is within about 20% error of simulation results, thus exerting no influence; the smaller the thickness, the smaller the influence. |
| Peeling thickness | Several mm to several cm | Maximum detectable peeling thickness : 1 cm or less | About 1 cm detection capability is sufficiently effective, because peeling of site to be repaired generally includes thin portion (1 cm or less) as well as portion more than 1 cm thick. | Based on simulation results (see Fig.3). |
| Cavity thickness | 0.1 mm to several mm | 0.1 mm ~ | Can deal with most peelings if detectable with cavity thickness of 0.1 mm. | Surface temperature difference due to peeling arises because air is lower in heat conductivity than concrete; thickness of cavity dose not affect heat conductivity of air layer. |

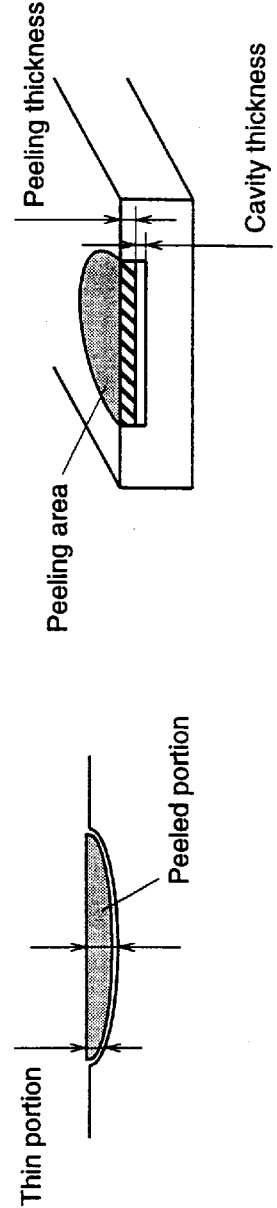

PEELING DETECTOR FOR TUNNEL WALL

BACKGROUND OF THE INVENTION

This invention relates to a peeling detector for a tunnel wall, which detects peeling of a wall of a tunnel while moving in the tunnel.

In inspecting a tunnel wall peeling, it has been customary practice to beat the wall surface manually with a hammer or the like, hear the sounds, and locate the site of peeling based on differences in sound.

Among methods for detecting the peeling of a concrete structure by use of infrared radiation is a method for detecting the difference in temperature between a peeled part and a normal part that occurs because of a change in the ambient temperature. This method has been used mainly in the inspection of a bridge footing or a building wall surface.

With the above-described hammering test of the tunnel wall, this wall is so wide that the sounding of the entire wall takes an enormous time.

The testing method using infrared rays poses the following problem: The interior of a tunnel is a closed space, and unlike a bridge footing or a building wall, is free from changes in the ambient temperature or exposure to sunlight throughout the day. In a natural condition, there is no difference in the wall temperature between the peeled part and normal part. Thus, the infrared (IR) method was not applicable to the inspection of the tunnel wall.

SUMMARY OF THE INVENTION

The object of the present invention is therefore, to provide a peeling detector for a tunnel wall, the detector being capable of rapidly inspecting the tunnel wall with the effective use of infrared radiation.

To attain the above object, the peeling detector for a tunnel wall related to the present invention comprises: heating means for uniformly heating a tunnel wall from the surface side by use of a light emitting heater such as an infrared lamp; and infrared radiation detecting means for detecting infrared radiation radiated from the tunnel wall by an infrared camera and producing a predetermined output relevant to the presence or absence of peeling of the tunnel wall, the heating means and the infrared camera being provided on a vehicle to heat and inspect the tunnel wall while moving.

When the light emitting heater heats the face of the tunnel wall while moving, the temperature of the face of the tunnel wall surface rises, causing a flow of heat from the face toward the back of the wall surface. If a cavity due to peeling is present in the interior of the wall surface, this flow of heat is interrupted by the cavity. As a result, the flow of heat at a site where peeling exists is slower compared with the flow of heat at a site where peeling does not exist. Thus, the surface temperature after heating lowers more slowly at the former site than at the latter site. Consequently, the wall temperature is higher at the site with peeling than at the site without peeling.

The heating-associated difference in wall temperature is detected by the infrared camera as temperature distribution images. These temperature distribution images are image processed by a computer, and outputted in the form of, say, a map showing the presence and/or absence of peeling in the tunnel wall. Without image processing, an inspector may directly observe the temperature distribution images on a display such as TV monitor, and judge whether peeling exists or not in the wall surface.

BRIEF DESCRIPTION OF THE DRAWINGS

FIG. 3 is a development view exemplifying the output of the inspection results obtained by inspecting the tunnel using the detector of FIG. 1;

FIG. 4 is an explanation drawing showing a comparison of heating methods;

FIG. 8 is an explanation drawing comparing the general characteristic of peeling of a tunnel wall 1, the detection limit of the inventive detector estimated from FIGS. 5, 6, and 7, and the results of evaluation of the effectiveness of the peeling detection capability of the detector, each item being described in relation to the peeling area, peeling thickness and cavity thickness.

DETAILED DESCRIPTION OF THE PREFERRED EMBODIMENTS

Preferred embodiments of a peeling detector for a tunnel wall surface of the present invention will now be described in detail by reference to the drawings.

Figure 1:
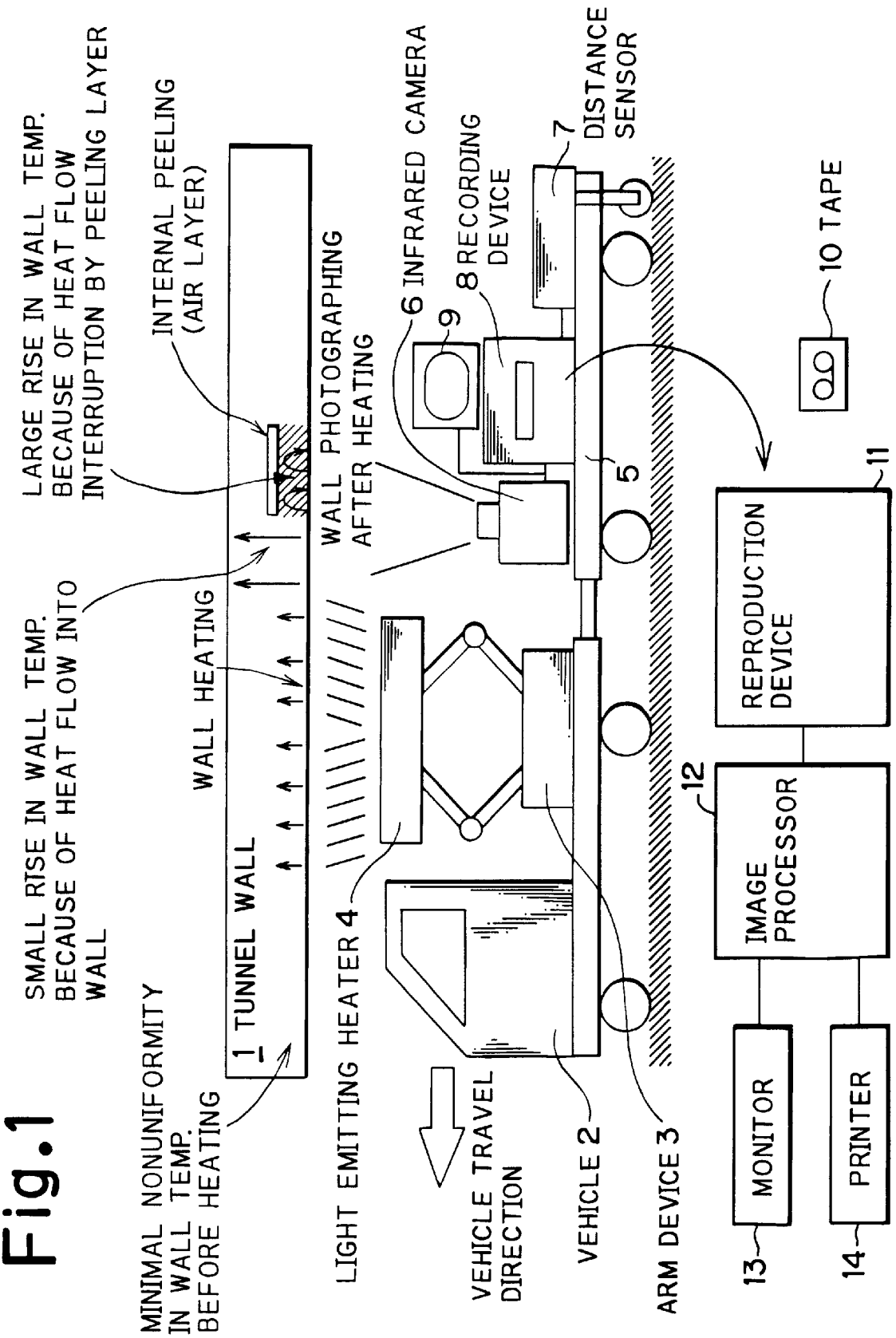
FIG. 1 is a schematic structural view of a peeling detector for a tunnel wall showing an embodiment of the present invention.

FIG. 1 is a schematic structural view of a peeling detector for a tunnel wall surface showing an embodiment of the present invention.

As illustrated in FIG. 1, a light emitting heater 4 (e.g., an infrared lamp) is mounted on a self-propelled vehicle 2 via an extendible arm device 3 to inspect a tunnel wall 1. A truck 5 pulled by this vehicle 2 is mounted with an infrared (IR) camera 6 for measuring infrared radiation radiated by the tunnel wall 1; a distance sensor 7 for measuring the distance traveled by the vehicle 2 and the truck 5; a recording device 8 for recording temperature distribution images obtained by the infrared camera 6, and data on mileage obtained by the distance sensor 7; and a display device 9 indicating, in real time, the temperature distribution images obtained by the infrared camera 6.

In the recording device 8, the temperature distribution images and mileage data recorded on a tape 10 are reproduced by an external reproduction device 11, and processed by an image processor (computer) 12. In the drawing, the numerals 13 and 14 denote a monitor and a printer, respectively, for the image processor 12.

Figure 2:
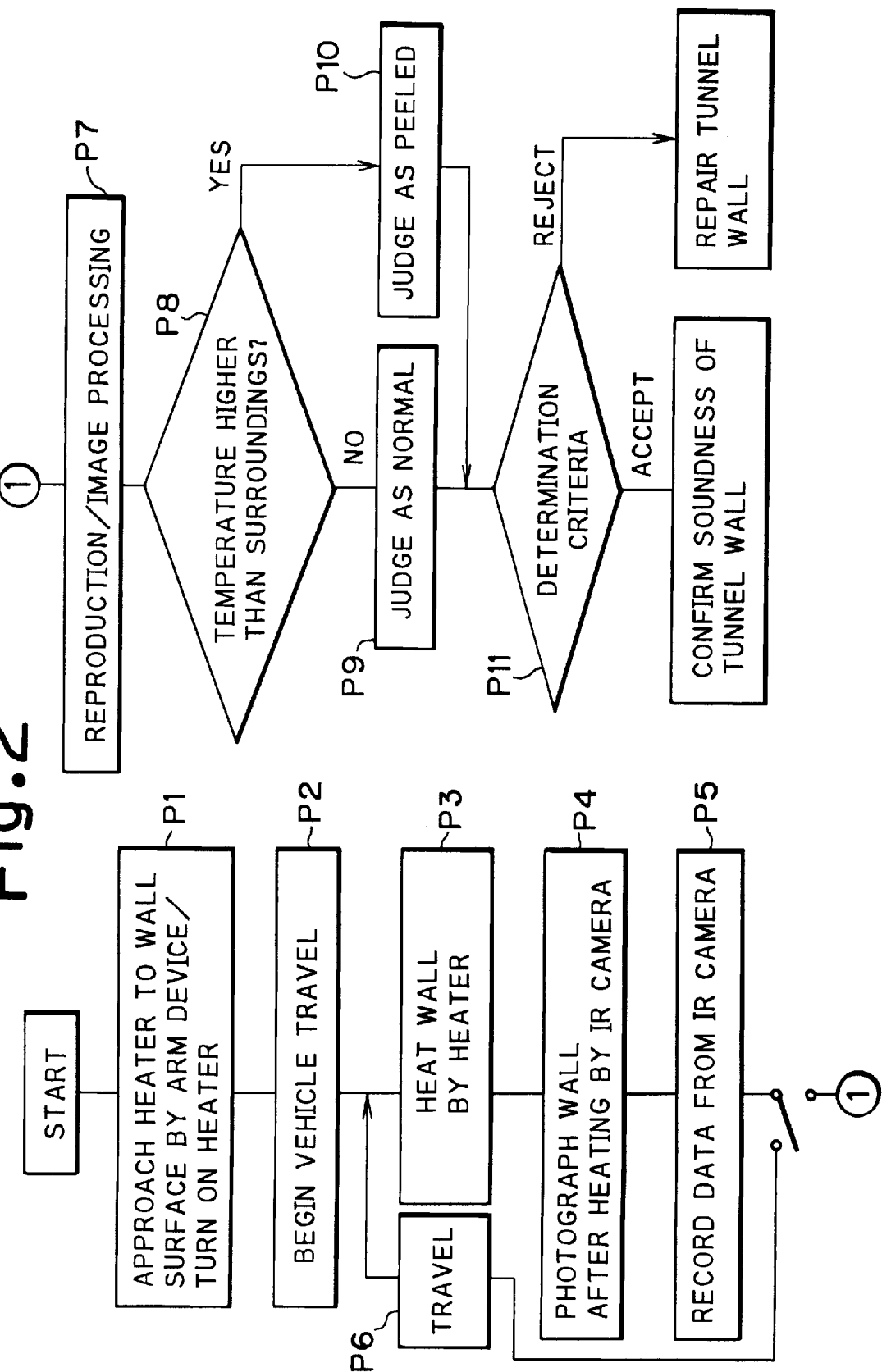
FIG. 2 is a flow chart showing an example of the procedure for inspecting the tunnel wall by the detector of FIG. 1.

FIG. 2 is a flow chart showing an example of the procedure for inspecting the tunnel wall surface by the detector of FIG. 1;

According to this flow chart, the light emitting heater 4 approaches to the tunnel wall 1 by the arm device 3 for the efficient heating of the tunnel wall surface 1, whereafter the heater 4 is turned on (Step P1).

Then, the vehicle 2 starts running at a constant speed while pulling the truck 5 (Step P2). As will be described later, the distance between the light emitting heater 4 and the infrared camera 6 should be as long as possible. According to the instant embodiment, therefore, the light emitting heater 4 is provided on the vehicle 2, while the infrared camera 6 is provided on the truck 5, so that it becomes easy to secure a long distance between the two members.

As the vehicle 2 moves, the tunnel wall 1 is sequentially heated uniformly by the light emitting heater 4 (Step P3). The wall after heating is photographed by the infrared camera 6, proceeding behind the light emitting heater 4, a constant period of time after heating (Step P4). The constant period of time from heating until photographing depends on the moving speed of the vehicle 2 and the distance between the light emitting heater 4 and the infrared camera 6.

The temperature distribution images obtained by the infrared camera 6, and the mileage data obtained by the distance sensor 7 are recorded by the recording device 8 (Step P5).

Upon completion of measurement, the travelling of the vehicle (Step P6) is stopped, and the tape 10 is withdrawn from the recording device 8. The data on the tape 10 are analyzed by the reproduction device 11 and the image processor 12 (Step P7). In the reproduced temperature distribution images, the portions higher in temperature than the surroundings are judged as peeled, and other portions as normal (Steps P8, P9, P10).

The results of judgment on peeling can be outputted as a development view as shown in FIG. 3 along with the simultaneously reproduced data from the distance sensor 7. In accordance with certain criteria including the results of judgment, the magnitude of peeling and the denseness of peeling, the soundness of the tunnel wall surface 1 is evaluated to determine whether to repair the tunnel wall surface 1 or not (Step P11).

In the instant embodiment, the light emitting heater 4 is used to heat the tunnel wall 1. For information, a comparison of this method with other heating methods is shown in FIG. 4. FIG. 4 demonstrates that the light emitting heater 4 is the most suitable tool for inspection while in motion.

Next, the effectiveness of the detector of the above-described construction, according to the preferred embodiment of the present invention, will be described.

Figure 5:
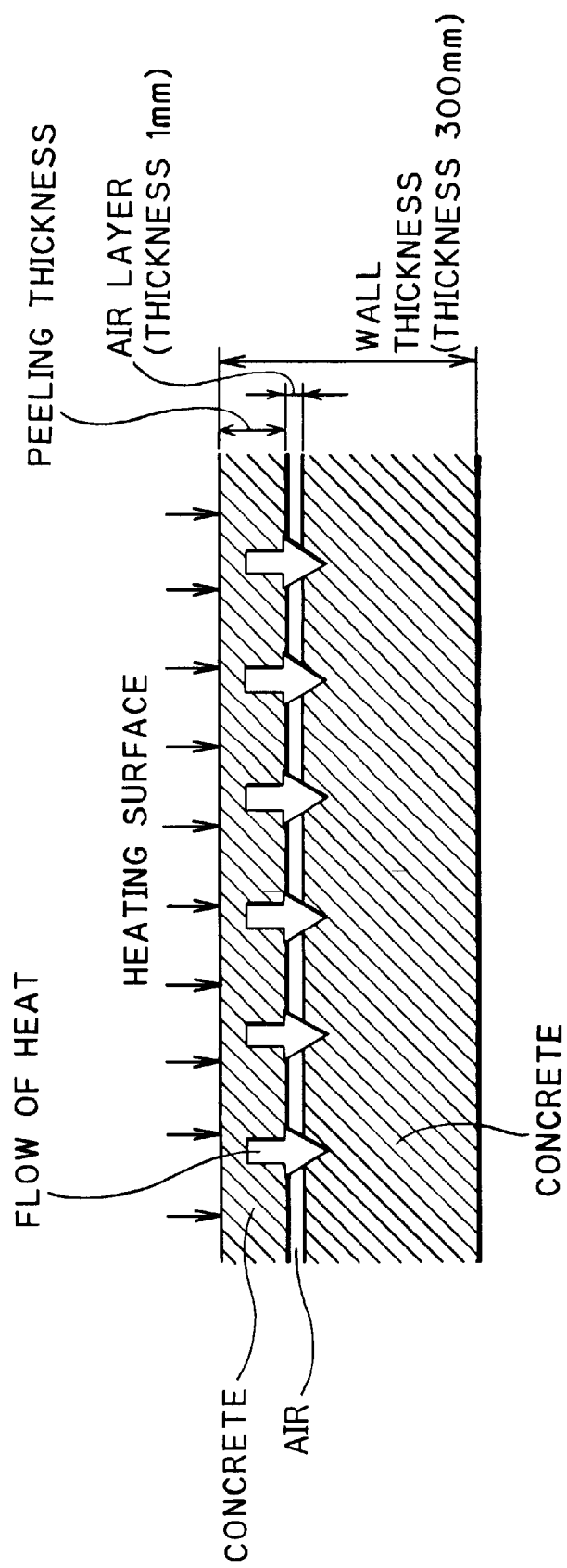
FIG. 5 is a simulation model used in the calculation of the difference in temperature that occurs between a normal portion and a peeled portion upon heating with a light emitting heater.

FIG. 5 is a simulation model used in the calculation of the difference in temperature that occurs between a normal portion and a peeled portion upon heating with the light emitting heater 4. According to this model, the tunnel wall 1 was assumed to be an infinite flat, and peeling was assumed to spread infinitely with a constant thickness in the wall. The flow of heat was considered as occurring only in the direction of the wall thickness during heating on the wall surface with a constant energy density. Given these assumptions and consideration, the computer set up an equation of one-dimensional heat conduction. Behind the peeling, an air layer 1 mm thick was assumed to be present.

The physical properties of concrete were used for the wall, while the physical properties of air were used for the air layer. These properties were set at the following values, and used for calculation:

| | |
|---|---|
| Wall: | Density 2100 kg/m$^3$, specific heat 0.879 kj/kg° C., heat conductivity 1.00 W/m ° C. |
| Air layer: | Density 1.16 kg/m$^3$, specific heat 1.01 kj/kg° C., heat conductivity 0.0257 W/m ° C. |

Figure 6:
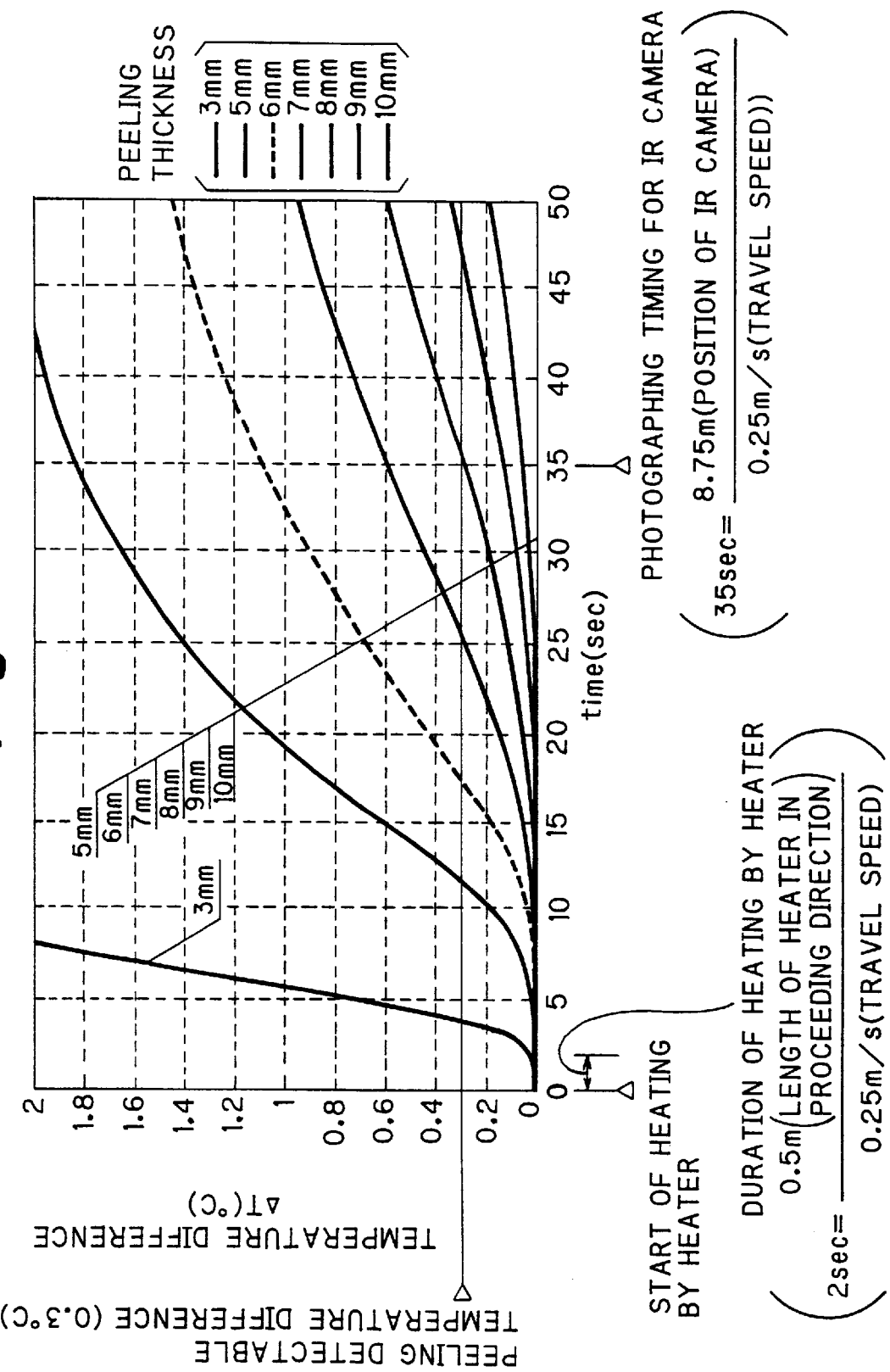
FIG. 6 is a graph of an example in which the temperature differences between normal and peeled portions were calculated using the simulation model of FIG. 5.

FIG. 6 shows an example in which the temperature differences between normal and peeled portions were calculated using the above calculation method. Heating was performed using the inventive detector, and the specifications for the detector were set at the following values:

Travel speed: 1 km/h (0.25 m/s)

Position of IR camera: 8.75 m behind heater

Heater size: 0.5 m (proceeding direction)×2.0 m (direction perpendicular to proceeding direction)

Heater output: 60 kW

Efficiency of heat conduction from heater to wall surface: 50%

Temperature resolution of IR camera: 0.025° C.

The interior of the tunnel is free from changes in the ambient temperature or influences from sunlight. Thus, the tunnel wall 1 has a uniform temperature distribution before heating with the light emitting heater 4. After uniform heating with the light emitting heater 4, it is only the peeled portion that has a higher temperature than the surroundings. If the difference in temperature of the peeled portion is sufficiently high compared with the temperature resolution of the infrared camera 6, therefore, it is possible to identify the peeled portion.

The temperature resolution of the infrared camera 6 is 0.025° C. In FIG. 6, therefore, the temperature difference detectable as peeling by the infrared camera 6 was set at 0.3° C. (12 times the temperature resolution). Based on the position of the infrared camera 6 and the travel speed, the photographing timing of the infrared camera 6 was found to be 35 seconds (=8.75/0.25) after the start of heating.

The above results given in FIG. 6 show that the thickness of peeling detectable under the above-described calculation conditions is about 8 mm.

Figure 7:
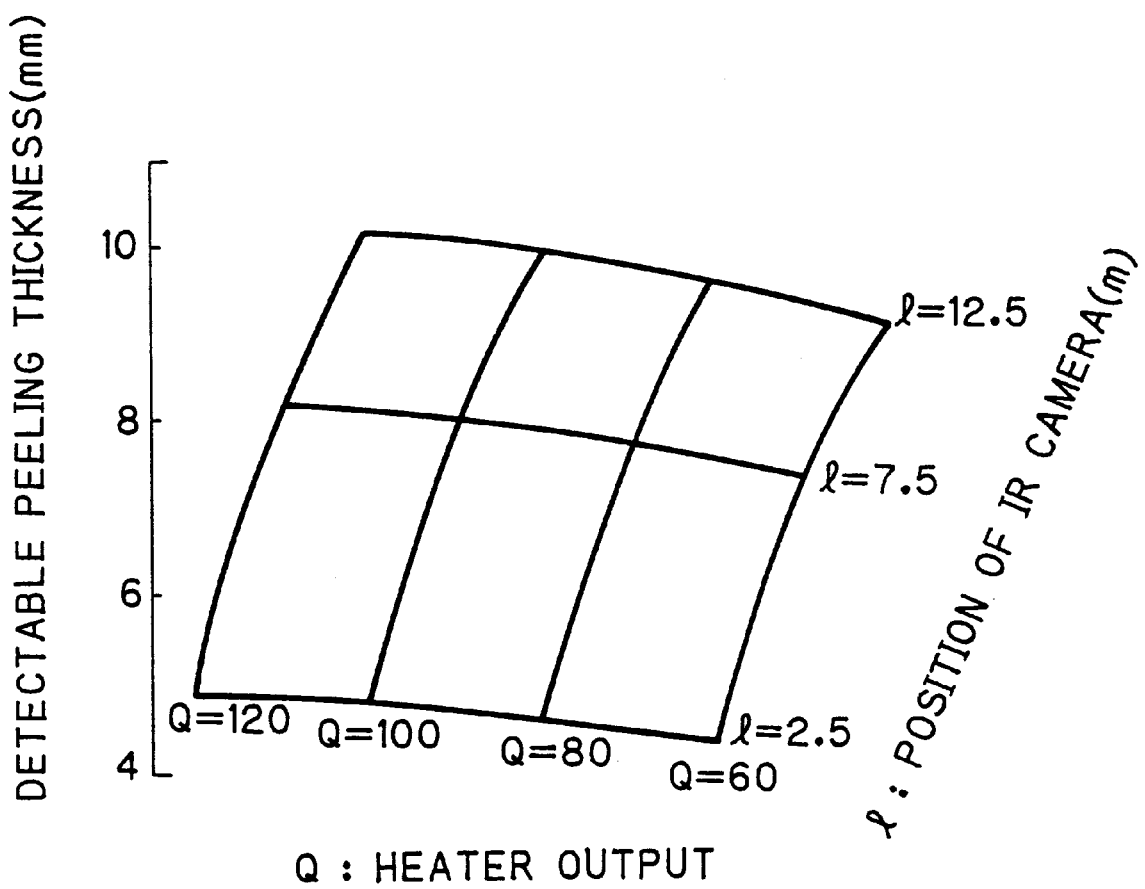
FIG. 7 is a graph of an example in which the detection limits of the detector of FIG. 1 were calculated with the specifications for the detector as parameters by use of the simulation model of FIG. 5.

In view of the calculation process in FIG. 6, one will see that the detectable peeling thickness for the inventive detector depends on the specifications for the detector, such as travel speed. FIG. 7 shows the results of calculation of the detectable peeling thickness using the following specifications for the detector:

Travel speed: 1 km/h (0.25 m/s)

Position of IR camera: 2.5 m, 7.5 m, 12.5 m behind heater

Heater size: 0.5 m (proceeding direction)×2.0 m (direction perpendicular to proceeding direction)

Heater output: 60 kW, 80 kW, 100 kW, 120 kW

Efficiency of heat conduction from heater to wall surface: 50%

Temperature resolution of IR camera: 0.025° C. (temperature difference detectable as peeling: 0.3° C.)

From FIG. 7, one will see that when the infrared camera 6 is positioned 12.5 m behind the heater, a peeling with a thickness of about 1 cm can be detected, although depending on the heater output. One will also see that as the infrared camera 6 is moved more rearward of the light emitting heater 4, or as the heater output is increased, the detectable peeling thickness tends to become larger.

FIG. 8 shows the general characteristics of peeling of the tunnel wall 1, the detection limits of the inventive detector estimated from FIGS. 5, 6, and 7, the evaluation results on the effectiveness of the peeling detecting capability of the inventive detector, in relation to each of the items, peeling area, peeling thickness, and cavity thickness. From FIG. 8, the inventive detector is found effective for detecting the peeling of the tunnel wall 1.

Of the calculation conditions for FIGS. 6 and 7, the width of the light emitting heater 4 in the direction perpendicular to the proceeding direction is as small as 2 m. In this case, the range of heating by the light emitting heater 4 may be too narrow to inspect the whole of the tunnel wall surface 1 during a single travel. However, several travels at the same places with the heating position being shifted enable the entire tunnel wall surface 1 to be inspected.

The detector of the present invention, as described above, can markedly increase the inspection speed in comparison with a conventional hammering inspection method by making an inspection using an infrared camera while moving.

Furthermore, the inventive detector moves while heating a tunnel wall using a light emitting heater. Thereby, the detector can cause a difference in the wall temperature to the tunnel wall which has small fluctuations in ambient temperature and which, under natural conditions, generates no difference in the wall temperature between a peeled portion and a normal portion. Thus, the invention can apply an infrared inspection method to the inspection of a tunnel wall.

What is claimed is:

1. A peeling detector for detecting peeling formed inside a tunnel wall, comprising:

heating means for uniformly heating inside a tunnel wall by irradiating heat towards a tunnel wall surface by a heater;

infrared radiation detecting means for detecting a first heat irradiated by a first portion of said tunnel wall and a second heat irradiated by a second portion of said tunnel wall;

comparing means for comparing the detected first heat and the detected second heat;

judging means for judging that a peel exists inside the first portion of said tunnel wall when the detected first heat is higher than the detected second heat;

evaluating means for evaluating at least one of a magnitude of peeling or a denseness of the peeling; and determining means for determining whether the tunnel wall is sound or is in need of repair based on a determination criteria and a result of said evaluating means, wherein the heating means and the infrared radiation detecting means are provided on a vehicle to heat and inspect the tunnel wall while moving.

2. The peeling detector of claim 1, wherein the light emitting heater is provided on the vehicle via an extendible arm device.

3. The peeling detector of claim 1, wherein a distance sensor for measuring the distance traveled by the vehicle is provided on the vehicle.

4. The peeling detector of claim 2, wherein a distance sensor for measuring the distance traveled by the vehicle is provided on the vehicle.

5. The peeling detector of claim 1, wherein the light emitting heater is provided on a self-propelled vehicle, and the infrared camera is provided on a truck pulled by the vehicle.

6. The peeling detector of claim 2, wherein the light emitting heater is provided on a self-propelled vehicle, and the infrared camera is provided on a truck pulled by the vehicle.

7. The peeling detector of claim 3, wherein the light emitting heater is provided on a self-propelled vehicle, and the infrared camera is provided on a truck pulled by the vehicle.

8. The peeling detector of claim 4, wherein the light emitting heater is provided on a self-propelled vehicle, and the infrared camera is provided on a truck pulled by the vehicle.

9. The peeling detector of claim 1, wherein said heating means is a light emitting heater.

10. A peeling detector for detecting peeling formed inside a tunnel wall, comprising:

heating means for uniformly heating inside the tunnel wall by irradiating heat towards a tunnel wall surface by a heater;

infrared radiation detecting means for detecting a first heat irradiated by a first portion of said tunnel wall and a second heat irradiated by a second portion of said tunnel wall;

first comparing means for comparing the detected first heat and the detected second heat;

judging means for judging that a peel exists inside the first portion of said tunnel wall when the detected first temperature is higher than the detected second temperature;

evaluating means for evaluating at least one of a magnitude of peeling or a denseness of the peeling; and determining means for determining whether the tunnel wall is sound or is in need of repair based on a determination criteria and a result of said evaluating means.

* * * * *